(12) United States Patent
Bhambhani et al.

(10) Patent No.: US 9,782,470 B2
(45) Date of Patent: Oct. 10, 2017

(54) METHOD OF OBTAINING THERMOSTABLE DRIED VACCINE FORMULATIONS

(71) Applicant: Merck Sharp & Dohme Corp., Rahway, NJ (US)

(72) Inventors: Akhilesh Bhambhani, Doylestown, PA (US); Robert K. Evans, Bangor, ME (US); Jessica Sinacola, Collegeville, PA (US); Morrisa Jones, Upper Darby, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/029,060

(22) PCT Filed: Oct. 13, 2014

(86) PCT No.: PCT/US2014/060222
§ 371 (c)(1),
(2) Date: Apr. 13, 2016

(87) PCT Pub. No.: WO2015/057541
PCT Pub. Date: Apr. 23, 2015

(65) Prior Publication Data
US 2016/0228532 A1    Aug. 11, 2016

Related U.S. Application Data

(60) Provisional application No. 61/891,527, filed on Oct. 16, 2013.

(51) Int. Cl.
*A61K 39/12* (2006.01)
*C12N 7/00* (2006.01)
*A61K 9/19* (2006.01)
*A61K 47/26* (2006.01)
*A61K 9/00* (2006.01)
*A61K 9/14* (2006.01)
A61K 47/18 (2017.01)
A61K 39/00 (2006.01)

(52) U.S. Cl.
CPC ............ *A61K 39/12* (2013.01); *A61K 9/0019* (2013.01); *A61K 9/145* (2013.01); *A61K 9/19* (2013.01); *A61K 47/26* (2013.01); *C12N 7/00* (2013.01); *A61K 47/183* (2013.01); *A61K 2039/525* (2013.01); *A61K 2039/55505* (2013.01); *A61K 2039/70* (2013.01); *C12N 2710/20034* (2013.01); *C12N 2710/20071* (2013.01)

(58) Field of Classification Search
None
See application file for complete search history.

(56) References Cited

U.S. PATENT DOCUMENTS

| | | |
|---|---|---|
| 4,389,794 A | 6/1983 | Bitterly |
| 4,664,924 A | 5/1987 | Sugisawn et al. |
| 4,809,596 A | 3/1989 | Akutsu et al. |
| 4,882,851 A | 11/1989 | Wennerstrum et al. |
| 5,565,318 A | 10/1996 | Walker et al. |
| 6,128,321 A | 10/2000 | Bennett et al. |
| 6,956,865 B1 | 10/2005 | Khaunte et al. |
| 7,101,693 B2 | 9/2006 | Cicerone et al. |
| 2010/0015180 A1 | 1/2010 | Francon et al. |
| 2010/0218395 A1 | 9/2010 | Durante et al. |
| 2010/0297231 A1 | 11/2010 | Vehring |
| 2011/0209354 A1 | 9/2011 | Durance et al. |
| 2011/0243988 A1 | 10/2011 | Ohtake et al. |
| 2012/0291305 A1 | 11/2012 | Fu et al. |
| 2013/0189304 A1 | 7/2013 | Truong-Le |

FOREIGN PATENT DOCUMENTS

| | | |
|---|---|---|
| WO | WO02103407 A2 | 12/2002 |
| WO | WO2009033285 A1 | 3/2009 |
| WO | WO2009049409 A1 | 4/2009 |
| WO | WO2009109550 A1 | 9/2009 |
| WO | WO2013010257 A1 | 1/2013 |
| WO | WO2014009328 A1 | 1/2014 |
| WO | WO2015057540 A1 | 4/2015 |
| WO | WO2015057548 A1 | 4/2015 |

OTHER PUBLICATIONS

Bhambhani, Akhilesh; "Lyophilization Strategies for Development of a High-Concentration Monoclonal Antibody Formulation: Benefits and Pitfalls"; Am. Pharm. Review; 2010; 31-38; 13(1).
Seo, Jeong-Ah, et al.; "Making monosaccharide and disaccharide sugar glasses by using microwave oven"; Journal of Non-Crystalline Solids; 2004; 111-114; 333.
Wy Chiang et al., A Microwave Applicator for Uniform Irradiation by Circularly Polarized Waves in an Anechoic Chamber, Rev Sci Instrum, Aug. 2014, pp. 084703-1-084703-5. vol. 85.
James P. Dolan et al., Use of Volumetric Heating to Improve Heat Transfer During Vial Freeze-Drying, Dissertation submitted to the Faculty of the Virginia Polytechnic Institute and State University in partial fulfillment of the requirements for the degree of Doctor of Philosophy in Mechanical Engineering, Sep. 1998, https://theses.lib.vit.edu/theses/available/etd-82298-16291-unrestricted/etd_2008.pdf.
T. Durance et al, 2011, Microwave Dehydration of Food and Food Ingredients, In: Murray Moo-Young (ed.), Comprehensive Biotechnology, Second Edition, vol. 4, pp. 617-628.

*Primary Examiner* — Shanon A Foley
(74) *Attorney, Agent, or Firm* — Henry P. Wu; Gloria M. Fuentes (57) ABSTRACT

This present invention relates to compositions and methods for stabilizing a dried vaccine formulations. In particular, the invention provides a method for producing a vaccine composition comprising the steps of providing an aqueous composition comprising a buffer, the vaccine components and between 17.5% w/w and 60% w/w of a non-polymeric sugar, freezing the composition, and applying microwave radiation under a pressure lower than atmospheric pressure in order to sublimate the composition and obtain a dried vaccine formulation. The invention also provides a product obtainable by this method.

20 Claims, 2 Drawing Sheets

METHOD OF OBTAINING THERMOSTABLE DRIED VACCINE FORMULATIONS

FIELD OF THE INVENTION

The present invention relates to methods of drying vaccines in a primary container utilizing microwave vacuum drying in a protective matrix comprising a sugar for the formation of a thermostable formulation through sublimation. The resulting formulations are suitable for storage, and subsequent parenteral usage and/or oral delivery.

BACKGROUND OF THE INVENTION

Vaccines, including those containing live virus, inactivated virus, virus-like particles, viral protein subunits and combinations thereof, are thermolabile and to overcome the instability barrier, vaccine products are typically stored in a dried state. The labile nature of vaccines renders drying of vaccines a challenging task and often requires long conservative freeze-drying cycles (usually cycle times in excess 48-72 hrs) to obtain dried thermostable vaccines. Historical approaches to obtain dried vaccine and biologics hinges mostly on the use of lyophilizer and to a limited extent on spray-drying. However, vaccines, even if dried using these methods, have thus far failed to achieve adequate long-term room temperature stability.

Lyophilization (freeze-drying) processes typically entail freezing the vaccine components and then drying by sublimation. Removal of the solvent and substitution by a matrix comprising protective molecules such as sugar molecules, may increase the stability of the protein by preventing degradation and denaturation of this protein. U.S. Pat. No. 5,565,318 describes the use of a polymeric sugar as a protective agent in the formation of room temperature stable semi-spheres containing biologicaly active materials. U.S. Patent Application Publication No. 20100297231 describes foam-forming formulations comprising a biologically active protein and a polyol. U.S. Patent Application Publication No. 20110243988 describes the use of polyols as a stabilizer for dry powder live virus vaccines. International Patent Application Serial No. PCT/EP2013/064422 describes the preservation of biologically active protein by freeze-drying in a protective matrix comprising a sugar.

Microwave vacuum-drying is a rapid method that can yield products, such as foods, plants and biological materials, with improved stability compared to air-dried and freeze-dried products. Because the drying is done under reduced pressure, the boiling point of water and the oxygen content of the atmosphere is lowered, so food or medicinal components sensitive to oxidation and thermal degradation can be retained to a higher degree than by air-drying. See, e.g., U.S. Pat. Nos. 4,389,794; 4,664,924; 4,809,596; 4,882,851; 6,128,321; 6,956,865; and International Patent Application Publication Nos. WO 02/103407; WO 2009/033285; WO 2009/049409; and WO2013/010257.

Seo et al., 2004, Journal of Non-Crystalline Solids, 333: 111-114 discloses a method for making sugar glass without caramelization of the sugar through the use of microwaves.

There is a desire for increased heat stability, especially in the developing world where transport, storage, and administration costs (mainly due to the need of continuous refrigeration, also referred to as the "cold chain") represent a significant portion of the product cost.

SUMMARY OF THE INVENTION

The present invention relates to a method for drying a vaccine formulation (preferably in less than 12 hours) resulting in a dried vaccine formulation with stability comparable to freeze-dried vaccine (which requires drying times greater than 24 hours). The method comprises a) providing a primary container containing an aqueous composition comprising 1) a buffer, 2) a live virus, inactivated virus, virus-like particle (VLP), a viral protein subunit or a combination thereof, and 3) between 17.5% w/w and 60% w/w of a non-polymeric sugar, b) freezing the primary container, and c) applying microwave radiation to the frozen pellet under a pressure below atmospheric pressure, e.g., in the range of 20 to 500 mTorr or 20 to 200 mTorr, to produce a dried pellet of substantially spherical shape in order to sublimate the composition and obtain a dried formulation. The method allows for drying by sublimation in short times, for example, less than 12 hours, and optimally in a range from 3 to 8 hours.

In certain embodiments, the pressure is reduced to a range from 20 to 500 mTorr or 20 to 200 mTorr or 20 to 100 mTorr or 20 to 70 mTorr. In certain embodiments, the temperature of the composition in said apparatus does not exceed 45° C. or 35° C. Typically, the moisture content of the composition after drying is less than 6.0%.

In certain embodiments, the amount of the sugar in the aqueous composition is from 20-55% w/w, 20-50% w/w, 20-47.5% w/w, 25-47.5% w/w, 30-47.5% w/w, 30-40% w/w, 25-35% w/w and 27-30% w/w. The sugar may comprise monomeric and/or dimeric molecules. In certain embodiments, the sugar is glucose, galactose, maltose, sucrose, trehalose, fructose, lactose, saccharose, mannitol, sorbitol, raffinose, cyclodextrin, hydroxyethyl starch, xylitol or a combination thereof.

The microwave radiation is provided in an amount sufficient to heat and dry the sample without adversely affecting the integrity of the virus. In certain embodiments, the microwave radiation is applied with a power density of between 0.5 and 8 Kilowatts/kg. In certain embodiments, the microwave radiation is applied in a continuous or semi-continuous mode. In yet other embodiments, the microwave radiation is applied in a traveling wave format. In certain embodiments, the power applied during one or more cycles is such that 20% of the total power is applied during the first half of the cycle with the remaining 80% of the total power applied during the second half of the cycle. The ratio of power distribution between the power used in first half cycle and total drying power is usually in 15%-50% range.

In an optional embodiment, the composition is frozen prior to applying the microwave radiation. The composition may be flash frozen, or shelf frozen at a slow (<0.5 C/min) or fast (>0.5 C/min) rate using methods known to those skilled in the art. See, e.g., Bhambhani et al., 2010, Am. Pharm. Review, 13(1):31-38.

In certain embodiments, the vaccine is a virus including a live virus. In certain aspects of this embodiment, the virus is an enveloped virus or a non-enveloped virus. The enveloped virus may be selected from cytomegalovirus (CMV), herpes simplex virus, measles, mumps, rubella, respiratory syncytial virus (RSV), Epstein-Barr virus, Rabies, Hepatitis C, Hepatitis B virus, Dengue Virus and varicella-Zoster virus. The non-enveloped virus may be selected from adenovirus, parvovirus, polio virus, Norwalk virus, and rotavirus.

In certain embodiments, the vaccine is a virus-like particle. Virus-like particle (VLP) based vaccines many be selected from vaccines for Hepatitis B, Chikungunya and human papillomavirus.

In certain embodiments, the vaccine is a combination vaccine. An example of a combination vaccine of live viruses is MMR (measles, mumps and rubella) and Proquad® (measles, mumps, rubella and varicella).

Other embodiments, aspects and features of the present invention are either further described in or will be apparent from the ensuing description, examples, and appended claims.

DETAILED DESCRIPTION OF THE INVENTION

The present invention relates to a method of obtaining dried vaccine formulations, in a container or in a cake form, comprising a live virus, inactivated virus, virus-like particle, viral protein subunit or a combination thereof, through the application of "radiant energy" (also known as microwave radiation or non-ionizing radiation), preferably, in a continuous or semi-continuous mode and in a traveling wave format, to the container or frozen cake of the vaccine formulation while maintaining the gross structure of frozen cake using sublimation as the predominant drying mechanism. The methods described herein are suitable for obtaining stable dried vaccines containing ≥20% sugar with improved drying efficiency (drying cycle time usually <12 hrs). Frozen cakes can be obtained by filling the container with the formulation and subjecting the container to freezing below the glass transition temperature (mostly >−40° C.) at slow and fast freezing rates (0.1-20° C./min) The microwave radiation is applied in a controlled manner in a vacuum chamber where the pressure is reduced below atmospheric pressure, to obtain the dried cake with no visible sign of boiling.

The present invention is based, in part, on the unexpected discovery that microwave vacuum drying of vaccines, particularly live enveloped viruses, can be achieved with minimal loss of immunogenicity through the use of high concentrations of disaccharide. Potency retention, despite the difference in drying pattern between lyophilization and microwave vacuum drying, is surprising for highly labile vaccine products such as Measles, Mumps, Rubella (MMR) and Varicella (VZV and VZVU where VZVU stands for urea containing formulation). The highly labile nature of the live enveloped virus vaccine (poor freeze/thaw yield, drying yield and stability) coupled with the potential for uneven heating in microwave (hot and cold spots due to higher dielectric constant and loss factor of water compared to ice) has made drying of live virus vaccines in microwave very difficult.

As disclosed in the Examples, microwave vacuum drying can be substituted for lyophilization for sensitive products such as vaccines based on enveloped live virus vaccines such as Varicella and MMR using the right combination of drying parameters and formulation. For example, faster drying and greater stability was observed for a microwave vacuum dried combination vaccine formulated in presence of high disaccharide in comparison to freeze-dried combination vaccine post 1 week incubation at 37° C. This was particularly surprising as the moisture of microwave vacuum dried formulation was significantly higher (5.5%) compared to freeze-dried formulation (1.0%). There is a general consensus in the freeze-drying field that products are more stable at lower moisture (usually in range of ≤3%) with a few exceptional cases in which an optimum moisture is preferred. Additionally, at higher moisture, in general, the stability is dramatically reduced especially at high incubation temperatures (37° C. in this case) due to a lower glass transition temperature. The microwave-dried cakes prepared using the methods of the invention are indistinguishable from a freeze-dried cake on a macroscopic level.

As another example, a high disaccharide formulation of an live virus vaccine (Vaccine 1 with 1 ml fill/3 cc vial) was dried in 7 hours in a microwave vacuum drying apparatus in contrast to 7 days in a lyophilizer. It should be noted that vaccine 1 has a freeze-drying yield of approximately 70% underlining the inherenet instability of the virus. Thus, it is surprising that comparable drying yield can be obtained using a radiative drying process with concomitant reduction in drying time. Faster sublimation allows for a higher throughput and a faster turnaround of drying space. Thus, use of microwave vacuum drying according to the methods of the present invention is preferred over lyophilization for efficient usage of cabinet space and greater flexibility.

Microwave drying provides a unique opportunity to achieve faster sublimation and in some cases alter the stability profile of thermolabile viruses by the virtue of an alternate heat transfer and mass transfer mechanism to the traditional approach. Furthermore, freeze-drying is considered an expensive unit operation due to significant capital investment, utility requirements and lengthy drying times. The lengthy drying times in freeze-drying are attributed to the fact that product temperature cannot be directly controlled during the primary drying as it depends on properties of container, formulation, shelf temperature, and chamber pressure of freeze-dryer system. Thus, a highly skilled scientist is required to perform a number of time-consuming experimental studies to obtain optimal lyophilization cycles and in most cases, sub-optimal" or "conservative" lyophilization cycles are used to dry sensitive products. The low temperature of freeze drying also does not guarantee stability post-drying due to denaturation at interfaces, cold denaturation or other freezing and drying stresses.

As used herein, the term "sublimation" refers to a process wherein materials change from a solid phase directly to a gaseous phase without passing through a liquid phase. With water, ice turns directly to water vapor without first melting to a liquid form, and then evaporating. Sublimation can occur at various temperatures and pressure combinations, but typically sublimation needs low temperatures and a vacuum pressure less than atmospheric. Sublimation provides advantages for materials processing as purity is maintained and the processed material does not have to be subjected to high temperatures, such as would be needed to boil off the water.

As used herein, the term "sugar" refers to any of a group of water-soluble carbohydrates of relatively low molecular weight. The term sugar includes reducing sugars (such as fructose and maltose), non-reducing sugars (such as sucrose and trehalose), sugar alcohols (such as xylitol and sorbitol) and sugar acids (such as gluconic acid and tartaric acid). A "non-polymeric sugar" refers to mono-, di-, tri-, and oligomeric sugar molecules comprising at most six monomeric sugar molecules.

All ranges set forth herein are intended to be inclusive of the lower and upper limit of the range. All values set forth 
herein can vary by ±1%, ±2%, ±5%, ±10%, ±15%, or ±20%, the term "about" is also meant to encompass these variations.

The methods of the invention are applicable to enveloped viruses, i.e., any virus in which the capsid is encapsulated within a phospholipid bilayer and non-enveloped viruses. Enveloped viruses may belong to any family of enveloped viruses, or a member thereof, including, but is not limited to, arenaviridae (e.g., LCM virus, Lassa virus and Junin virus), artcriviridac, asfarviridac, baculoviridac, bornaviridac, bunyaviridac (e.g., Bwamba virus, California encephalitis virus, sandfly fever virus and Rift Valley fever virus), coronaviridae (e.g., human coronavirus, aka SARS virus), filoviridae (e.g., Marburg virus and Ebola virus), flaviviridae (e.g., Yellow fewer virus, tick-borne encephalitis virus and hepatitis C virus), hepadnaviridae (e.g., hepatitis B-virus), herpesviridae (e.g., herpes simplex virus, varicella virus, cytomegalovirus and Epstein-Barr virus), iridoviridae, orthomyxoviridae (e.g., Influenza A and B viruses), paramyxoviridae (e.g., parainfluenza viruses, mumps virus, measles virus and respiratory syncitial virus), poxviridac (e.g., vaccinia, variola and smallpox), retroviridae (e.g., HTLV and human immunodeficiency virus), rhabdoviridae (e.g., vesicular stomatitis virus and rabies virus), and togaviridae (e.g., Chikangunya virus, Rubella virus and Sindbis virus). Non-enveloped viruses include Reovirdea (e.g., Rotavirus, Reovirus), Picornaviridae (e.g., poliovirus, Erbovirus), Adenoviridae (e.g., Adenovirus), Parvoviridae (e.g., Parvovirus B19, Canine Parvovirus) and Papovaviridae (e.g., Papillomavirus). These virus families are responsible for a wide variety of human and animal diseases including, but not limited to, encephalitis, gastro-intestinal disease, hemorrhagic disease, hepatitis, immunosuppressive diseases, ocular disease, pox (e.g. chickenpox, cowpox, smallpox, monkeypox, felinepox, swinepox, and pseudo-cowpox), respiratory disease, sexually transmitted disease, and cancer, and result in billions of infections, and millions of deaths, worldwide every year. Varicella, MMR, Rotavirus, HPV, DHPPi are examples of preferred live viruses.

The methods of the invention are also applicable to virus-like particles. Virus-like particle (VLP) based vaccines many be selected from vaccines for Hepatitis B, Chikungunya and human papillomavirus. Virus-like particle can be used at microgram quantities.

The methods of the invention are also applicable to vaccines comprising viral protein subunits. Examples of vaccines comprising viral protein subunits include Dengue vaccines. Viral protein subunits can be used at microgram quantities.

Accordingly, the present invention relates to a drying method that utilizes microwave radiation (also known as radiant energy or non-ionizing radiation) for the formation of dried vaccine products (<6% moisture) of a vaccine formulation through sublimation. In particular, in one embodiment, the present invention concerns a method of obtaining a dried vaccine, in a primary container such as a vial, dual cartridge device or syringe, through the application of microwave radiation in a traveling wave format to the vaccine formulation using sublimation as the predominant drying mechanism. The formulations are then subjected to microwave radiation in a controlled manner in a vacuum chamber to obtain the dried pellets/cake with no visible sign of boiling.

The buffer can be any carrier fluid suitable for dissolving and/or dispersing the substance to be carried. The buffer is usually selected from a pharmaceutically accepted buffer system. The preferred buffer is a pharmaceutically accepted buffer system with the ability to resist a change in pH upon addition of acid, base, inorganic compound, organic compound or other solvent or diluent. Buffering components, such as phosphate and citrate, are included to control the pH of the vaccine-containing solution, as well as to adjust the solution osmolarity. The buffer concentration may range from about 5 mM to about 2 M, with the pH of the solution adjusted to a range from about pH 4 to about pH 10.

A pharmaceutically acceptable buffer may be selected from the group consisting of potassium phosphate, sodium phosphate, sodium acetate, histidine, imidazole, sodium citrate, sodium succinate, ammonium bicarbonate, HEPES, Tris, Bis-Tris and a carbonate. The buffer may comprise a pH ranging from about pH 4 to about pH 10, a pH ranging from about pH 6 to about pH 8, and also, a pH of about pH 6 to about pH 7.

The sugar is generally selected from monomeric and/or dimeric molecules, and in particular can be chosen from the group consisting of glucose, galactose, maltose, sucrose, trehalose, fructose, lactose, saccharose, mannitol, sorbitol, xylitol, dextran and combinations thereof. The amount of the sugar in the aqueous composition may range from 20-55% w/w, 20-50% w/w, 20-45% w/w, 25-45% w/w, 25-47.5% w/w, 25-40% w/w, 30-47.5% w/w, 30-40% w/w, 25-35% w/w or 27-30% w/w. Preferably, the amount of sugar is higher than 25% w/w, typically around 27-40% w/w. In certain embodiments, the concentration of sugar is 17.5% w/w, 20% w/w, 25% w/w, 30% w/w, or 35% w/w.

The aqueous composition can further comprise surfactants, polymers, amino acids, and other pharmaceutically acceptable excipients. Polymer can be included to act as a stabilize for the virus. Polymer concentration may range from about 0.1% to about 20% (w/v). Surfactants can be included to decrease the surface tension and to displace the virus molecules from the surface. Surfactants may also increase the solubility of other formulation components. Surfactant concentration may comprise about 0.005% to about 2% by weight of said vaccine-containing formulation. Plasticizers may be included to increase the interaction of the glassy matrix with the virus vaccine upon dehydration, thereby enhancing storage stability. See e.g., U.S. Pat. No. 7,101,693. The concentration of plasticizer in the present invention may comprise about 0.2% to about 5% by weight of the formulation. Divalent cations and amino acids can be included to stabilize the virus and to adjust the pH and the osmolarity of the solution. The divalent cation concentration may range from about 0.1 mM to about 100 mM and the amino acid concentration may range from about 0.1% to about 10% (w/v).

In one embodiment, the aqueous composition comprises live virus, a sugar, polymer, surfactant, amino acid and a buffer.

In another embodiment, the aqueous composition comprises a virus-like particle, a sugar, polymer, surfactant, amino acid and a buffer.

A polymer can be selected from the group consisting of gelatin, hydrolyzed gelatin, collagen, chondroitin sulfate, a sialated polysaccharide, water soluble polymers, polyvinyl pyrrolidone, actin, myosin, microtubules, dynein, kinetin, bovine serum albumin, human serum albumin, lactalbumin hydrolysate, and combinations thereof. A polymer can be present at a concentration ranging from about 0.1% to about 20% (w/v). In one embodiment, the polymer is gelatin present at a concentration ranging from about 0.5% to about 5% (w/v).

A surfactant can be selected from the group consisting of polyethylene glycol, polypropylene glycol, polyethylene glycol/polypropylene glycol block copolymers, polyethylene glycol alkyl ethers, polyethylene glycol sorbitan monolaurate, polypropylene glycol alkyl ethers, polyethylene glycol/polypropylene glycol ether block copolymers, polyoxyethylenesorbitan monooleate, alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde and phenol, lignin-sulfite waste liquor, alkyl phosphates, quaternary ammonium compounds, amine, oxides, and betaines, wherein a surfactant is present at a concentration ranging from about 0.01% to about 2% by weight of said formulation. In one embodiment, the surfactant is polyoxyethylene sorbitan monooleate (polysorbate 80) at a concentration ranging from about 0.02% to about 0.5% by weight of said formulation.

A plasticizer can be selected from the group consisting of glycerol, dimethylsulfoxide (DMSO), propylene glycol, ethylene glycol, oligomeric polyethylene glycol, sorbitol, and combinations thereof, wherein a plasticizer is present at a concentration ranging from about 0.1% to about 5% by weight of said formulation.

Divalent cation can be selected from the group consisting of a pharmaceutically acceptable salt of magnesium, zinc, calcium, manganese, and their combinations thereof, at a concentration preferably ranging from about 1 mM to about 5 mM. In one embodiment, the divalent cation is calcium at a concentration ranging from about 1 mM to about 5 mM.

Amino acid can be alanine, arginine, methionine, serine, lysine, histidine, glycine, glutamic acid, and combinations thereof, wherein an amino acid is preferably present at a concentration ranging from about 0.1% to about 10% (w/v) Amino acids can also be provided by enzymatic digests of proteins. For example, NZ-Amine, an enzymatic digest of casein, can be used to provide a combination of amino acids. In one embodiment, the amino acid is arginine present at a concentration ranging from about 1% to about 8% (w/v).

The aqueous composition can be in a primary container such as a vial, either glass or plastic/resin, a dual cartridge device, a foil pouch device or any other microwave compatible device. A typical load to be placed in the microwave drying apparatus is 50-200 vials of 0.5 ml-1 l fill in a 3 cc vial with a maximum capacity of the instrument of 300-350 3 cc or 2 R vials. The total vial load is a function of microwave apparatus design.

In an optional embodiment, the aqueous composition can be pre-cooled. In the pre-cooling step, the composition is cooled to a temperature above the nucleation point and held at that temperature for a certain period of time. Pre-cooling is intended to minimize temperature gradients inter- and intra-vials and to assure uniform starting point to begin freezing and/or corresponding associated phase changes. Typical pre-cooling can occur at 1-5° C.

The microwave vacuum drying apparatus is capable of providing microwave radiation and a vacuum. Suitable apparatuses are described in U.S. Patent Application Publication Nos. US20120291305, US20100218395, and International Patent Application Publication No. WO 2013/010257. A suitable apparatus provides the required uniform drying at the required power application in the required time.

Microwaving refers to the use of non-ionizing electromagnetic radiation to actively induce the evaporation of polar molecules (e.g., water) from a biological composition. Microwaves are electromagnetic waves having operating frequencies anywhere from 0.3 GHz to 300 GHz. While frequencies anywhere within this range can be used, commercially available microwaves typically have frequencies of 2450 MHz and 915 MHz, both of which may be used, but 2450 MHz is preferred. The vibration of polar molecules in a constantly changing electrical field of microwave radiation increases the temperature of the system quickly. Increase of temperature is perhaps the most important factor associated with microwave radiation and the majority of the effects on biological materials are directly related to the heating effect.

A vacuum is pulled to produce a low pressure in the chamber of between 20 to 500 mTorr, 20 to 200 mTorr, 20 to 100 mTorr or 20 to 70 mTorr. Sublimation rate is directly proportional to the differential pressure between the ice-water interface and the chamber pressure and it is therefore preferred to use the highest achievable pressure differential and minimize the time and temperature required to dry the vaccine.

The level of vacuum also controls the temperature of the vaccine composition being dried. In certain embodiments, the reduced pressure also is utilized to ensure the temperature in the vacuum chamber during drying remains below 35° C.

Drying time is controlled by the amount of vacuum and the power applied to the vaccine composition in the chamber. The higher microwave power applied to the vaccine composition the shorter the required drying time, but if the power is too high for too long deactivation of a live virus can occur. Too low an application of microwave power applied to the vaccine composition is detrimental as it extends drying time. It is preferred to operate using the lowest vacuum pressure (and thus the lowest drying temperature) and the highest application of microwave power in the chamber provided the power is not applied to the extent to damage the vaccine composition being processed to complete the drying quickly while subjecting the vaccine composition to a minimum required drying temperature. In certain embodiments of the invention, the composition is sublimated in less than 12 hours. In other embodiments, the composition is sublimated in the range of 6 to 10 hours, or 3 to 8 hours.

The maximum output power of the microwave may vary in the range of 50 Watt (W) to 900 W per magnetron. Up to 8-16 magnetrons can be used. In one embodiment, the microwave maximum output power per magnetron may be 600 W. In another embodiment, the microwave maximum output power per magnetron may be 400 W (e.g., for a single run consisting of 50-200 vials).

Generally the microwave power applied will be in the range of between 0.5 and 8 KW/hr/Kg of the vaccine component being dried. The use of low power application is not preferred as the process may become too slow. Application of high power, i.e., above about 8 KW/Kg of the vaccine composition makes controlling the uniformity of the drying process at low moisture content more difficult. Generally an application of microwave power of about 4 KW/Kg of the vaccine composition is preferred.

It is also important to ramp up the microwave power to maintain the integrity of the vaccine composition. This can be achieved by slowly increasing the power at short intervals. Slower ramp (2 W/min) is preferred over stepping the power at bigger time interval (e.g. it is preferred to ramp up the power by 10 W every 10 min then going from 100 W to 250 W after 2.5 hrs). Such a ramping approach, in comparison to stepping up the power significantly, allows for gradual sublimation without compromising the product quality. In certain embodiments, the total energy in the first half of the cycle is only 15%, 20%, 25%, or 30% of the total energy required to dry the system. The ratio of power distribution between the power used in first half cycle and total drying power is usually in 15%-50%, 15-30%, or 15-20% range. Generally, to achieve the ramp up in microwave power, an initial cycle consists of a single magnetron. Additional magnetrons are added to the system as additional cycles are run. In general, any number of cycles can be used to provide the required microwave radiation. In certain embodiments, 3 to 8 cycles are used, for example 5 cycles, the cycle times are generally 30 minutes to 2 hours, and the total microwave energy output is generally in the range of 0.75 kWh to 8.0 kWh and is a function of total number of vials and product intrinsic characteristics.

In certain embodiments, the microwave radiation is applied in a continuous or semi-continuous mode or a batch mode. This selection is contingent on the process and product requirement. Semi-continuous and continuous mode allows for higher throughput while batch process may be used for an established apparatus design or a limited number of vial required.

As discussed above, the reduced pressure ensures that the temperature in the chamber is less than 40-45° C. In one embodiment, the temperature of the product is monitored does not exceed 35° C. The product temperature can be monitored using an IR sensor or a thermal imaging camera.

In certain embodiments, the microwave radiation is applied in a traveling wave format. With a traveling wave applicator, microwaves passes once through the sample. This results in better temperature control and uniform product drying. Less preferred is resonance cavity where microwaves pass multiple times through the sample. This results in thermal runaway (i.e. overheating) as the sample dries. A single pass microwave allows for controlling the product temperature by limiting the interaction between product and microwave. In contrast, electric field overlap in the resonance cavity results in an uncontrolled interaction and often results in the formation of hot and cold spots, uneven heating, and uneven sublimation of the product.

Under the conditions described herein, the moisture content of the composition after drying is less than 6.0%, less than 5.5%, or less than 5.0%. As discussed below, the relatively high moisture content is not detrimental to the formulations of the invention.

The vaccine composition is frozen prior to microwave vacuum drying. In embodiments of the invention where pre-cooling is used, freezing occurs after pre-cooling. It is preferable to freeze vaccine via flash freezing or fast freezing approach, especially for high disaccharide containing formulations, to minimize phase separation during freezing and/or potency loss due to extended time in solution for thermolabile vaccines.

The purpose of freezing is to (a) transform liquid solution phase to a frozen state (i.e., ice formation), (b) develop an ice structure and distribution in the frozen state to facilitate drying (i.e., porosity), and (c) crystallize the crystalline bulking agents to prevent unwanted crystallization during drying or storage (e.g., by annealing). Freezing is usually carried out below the glass transition temperature (Tg' for amorphous matrix) or below eutectic temperature (Teu for crystalline components) for sufficient period of time to allow complete transformation of liquid into a frozen solid state. Liquid solution can be converted to frozen state either using slow freeze (provides larger ice crystals), fast freeze (provides smaller ice crystals) or flash freeze.

Annealing (i.e., short-term re-heating of frozen product) is usually carried to allow efficient crystallization of bulking agent and/or water or to increase the size of ice crystals (Ostwald ripening). Annealing temperature is usually between Tg' and Teu of the bulking agent. In one embodiment, frozen pellets of vaccine are obtained by aliquoting the formulation (10 µl to 500 µl) on a chilled mold/surface (temperature <−100° C.). In another embodiment, frozen cakes are obtained by filling the container (e.g., a vial) with the formulation and subjecting the container to freezing (mostly <−40° C.) below the glass transition temperature at slow and fast freezing rate (0.1-20° C./min)

The final dried product may be reconstituted in an appropriate solution for administration of the vaccine to a patient.

The following examples serve only to illustrate the invention and its practice. The examples are not to be construed as limitations on the scope or spirit of the invention.

EXAMPLES

Example 1: Microwave Vacuum Drying (MVD) of Live Viral Vaccines (LVVs) in a Glass Vial A. LVV1: Enveloped Live Virus Vaccine (LVV1) in 5% Sucrose 2.5% Gelatin Phosphate Buffer in the Absence (PGS) and Presence of 1% Urea (PGSU)

Compatibility of LVV1 in 5% sucrose 2.5% Gelatin Phosphate buffer in the absence (PGS) and presence of 1% urea (PGSU) was evaluated in microwave vacuum drying as a function of cycle parameters. Table 1 lists the MVD parameters (vacuum pressure in all cases studied was in the range of 50-120 mTorr or less) and the corresponding moisture content for vial drying of LVV1, in presence and absence of urea. The microwave apparataus was used in a batch mode and consisted of four magnetrons. The power of each magnetron was contolled independently while the vacuum in the drying chamber was controlled by the a stand alone vacuum pump.

TABLE 1

MVD cycle parameters for LVV1, in absence (PGS) and absence of urea (PGSU)

| Active | S. No. | Image | Cycle Parameters | % Moisture |
|---|---|---|---|---|
| LVV1 in PGS | 1a | 0.5 ml/3 cc vial | 1 magnetron at 400 W for 1 hr 10 min<br>2 magnetrons at 400 W each for 2 hrs | 3.76 |
| | 1b | 0.7 ml/3 cc vial | 1 magnetron at 400 W for 1 hr<br>2 magnetrons at 400 W each for 2 hrs<br>1 magnetron at 400 W for 50 minutes | 4.37 |
| | 1c | 0.7 ml/3 cc vial | 1 magnetron at 400 W for 1 hr<br>2 magnetrons at 400 W each for 2 hrs<br>3 magnetron at 400 W each for 1 hr<br>1 magnetron at 400 W for 1 hr | 2.23 |

TABLE 1-continued

MVD cycle parameters for LVV1, in absence (PGS) and absence of urea (PGSU)

| Active | S. No. | Image | Cycle Parameters | % Moisture |
|---|---|---|---|---|
| | 1d | 0.7 ml/3 cc vial | 1 magnetron at 348 W for 1 hr<br>2 magnetron at 348 W each for 2 hrs<br>3 magnetron at 348 W each for 1 hr<br>1 magnetron at 348 W each for 1 hr | 2.9-4.3% |
| | 1e | 0.7 ml/3 cc vial | 1 magnetron at 348 W for 1 hr<br>2 magnetrons at 348 W each for 2 hrs<br>3 magnetrons at 348 W each for 3 hrs<br>2 magnetrons at 348 W each for 45 min | 2.79 ± 0.60% |
| LVV 1 in PGSU | 2a | 0.5 ml/3 cc vial | 1 magnetron at 400 W for 1 hr 10 min<br>2 magnetrons at 400 W each for 2 hrs | 2.21 |
| | 2b | 0.7 ml/3 cc vial | 1 magnetron at 400 W for 1.5 hr<br>2 magnetron at 400 W each for 1.5 hrs<br>3 magnetron at 400 W each for 55 minutes<br>4 magnetron at 400 W each for 1 hr<br>2 magnetron at 400 W each for 30 min | 1.46 |
| | 2c | 0.7 ml/3 cc vial | 1 magnetron at 400 W for 1 hr<br>2 magnetron at 400 W each for 2 hrs<br>1 magnetron at 400 W for 50 min | 2.47 |
| | 2d | 0.7 ml/3 cc vial | 1 magnetron at 300 W for 1 hr<br>2 magnetron at 300 W each for 1 hr<br>3 magnetron at 300 W each for 1.5 hr | 3.19 |
| | 2e | 0.7 ml/3 cc vial | 4 magnetron at 80 W each for 6 hrs | 2.44 |
| | 2f | 0.7 ml/3 cc vial | 1 magnetron at 123 W for 7 hrs | 3.44 |

To further study the impact of MVD on vaccine properties, drying yield and stability (both accelerated as well as long-term study) were determined. For comparison purposes a lyophilized control was included.

Consistency of MVD:

To verify drying consistency, 2 microwavable containers in a drying microwave chamber each containing 28 vials per container were dried and 15 samples were pulled from different locations throughout each container (experiment 1 d for Table 1) for relative potency testing with High-Throughput ELISA based potency assay. Samples were also analyzed for plaque potency using vaccine potency plaque assay. Plaque assay revealed the average adjusted potency for container #1 to be 129,607±31,348 pfu/mL while an average adjusted potency for container #2 to be 147,277±52,403 pfu/mL. Similarly, EIA assay revealed the average relative potency to be 0.46±0.08 U/ml post removing the high and lower corrected potency. Overall the potency per vial, in general, is consistent within a container and between container as observed using the high-throughput relative potency assay (RSD~17%) and traditional plaque assays (RSD~31%).

ELISA Infectivity Assay (EIA):

HFF-1 cells are planted on a 96 well plate. Twenty-four hours post planting, a serial dilution of the samples is done in the 96 well plate. Ninety-six hours post-infection, the plates are washed and fixed with 80% acetone. The plates are then blocked with a blocking buffer and incubated for one hour with 1° antibody [3F2(MK90-1) anti-gI] followed by a one hour incubation with 2° antibody [IgG(H+L)] conjugated with alkaline phosphates. Following antibody incubations, p-Nitrophenyl Phosphate (PNPP) substrate is added which reacts with alkaline phosphates to give a yellow product. The reaction is stopped after 30 minutes using sodium hydroxide (NaOH).

A spectramax plate reader is then used to read the absorbance at 405 nm. The data is fitted to a 4 Parameter logistic fit to obtain relative potency to the reference standard.

Short-Term Stability:

stability at 25° C. of LVV1 high solid (17.5% Sucrose/12.5% Trehalose) in 2.5% Gelatin Phosphate buffer (LVV1-ST30) vials (0.7 ml/2 R vials) dried in the microwave vacuum drier were obtained under different MVD cycles described below. LVV1, both MVD and freeze-dried, in PGS was used as a control in this study and all vials were incubated at 25° C. for 1 day, 4 days and 14 days. Lyophilization parameters used for the freeze-drying are listed in Table 2. Post incubation, the vials were analyzed using the relative potency assay. Results shown in Table 4.

TABLE 2

MVD conditions

| Sample | Cycle | Moisture (%) | Observations |
|---|---|---|---|
| LVV1 in PGS | 1 magnetron, 348 W, 1 hr<br>2 magnetrons, 348 W, 2 hrs<br>3 magnetrons, 348 W, 1 hr 20 mins<br>2 magnetrons, 348 W, 30 min<br>Total time: 4 hrs 50 min<br>50-100 mTorr | 2.3 | Final Temperature: 30-31° C. |
| LVV1-ST30 Cycle 1 | 1 magnetron, 30 W, 2 hrs<br>1 magnetron, 130 W, 1 hr<br>2 magnetrons, 130 W, 1 hr<br>3 magnetrons, 230 W, 1 hr<br>2 magnetrons, 230 W, 1 hr<br>Total Time: 6 hrs<br>50-100 mTorr | 5.7 | Final Temperature: 30° C. |
| LVV1-ST30 Cycle 2 | 1 magnetron, 30 W, 2 hrs<br>3 magnetrons, 90 W, 0.5 hrs<br>2 magnetrons, 150 W, 1 hrs<br>2 magnetrons, 260 W, 1 hr<br>2 magnetrons, 460 W, 1 hr<br>3 magnetrons, 702 W, 2 hrs<br>2 magnetrons, 580 W, 0.5 hrs<br>Total time: 9 hrs<br>50-100 mTorr | 3.7 | Final Temperature: 34° C. |

For comparison, a freeze-dried sample was added as control using the following cycle parameters as shown in Table 3.

TABLE 3

Freeze-Drying parameters

|  | Primary |  | Storage |
| --- | --- | --- | --- |
| Temperature (° C.) | −50 | −35 | −50 |
| Ramp Rate (° C./min) | 0 | 0.5 | — |
| Hold Time (min) | 60 | 10080 |  |
| Vacuum (mTorr) | 54 | 54 | 54 |

The results of this study indicate that the drying yield is lower for LVV1-ST30 for cycle 1 as compared to LVV1. The observed difference could be attributed to the MVD cycle difference as the LVV1 cycle is a high power cycle from the beginning while the LVV1-ST30 cycle requires a ramping of the power. Ramping was found to prevent the vials from "puffing" during drying. However, this may mean that these samples dry slower and this difference may be reflected in the potency differences seen in the results. Additionally, the residual moisture was greater in the LVV1-ST30 samples as compared to the LVV1 samples, 5.2% for LVV1-ST30 and 2.9% for LVV1.

TABLE 4

Drying yield and stability results

|  |  | Average | Std. Dev. | N | Std. Error |
| --- | --- | --- | --- | --- | --- |
| LVV1 MVD | Drying Yield | 69.5% | 27.3% | 6 | 11.2% |
|  | 1 Day @25 C. | 88.8% | 56.5% | 6 | 23.1% |
|  | 3 Days @25 C. | 51.3% | 27.3% | 6 | 11.1% |
|  | 7 Days @25 C. | 29.5% | 14.6% | 6 | 6.0% |
|  | 14 Days @25 C. | 21.8% | 13.6% | 6 | 5.5% |
| LVV1-ST30 MVD Cycle 1 | Drying Yield | 38.5% | 8.6% | 6 | 3.5% |
|  | 1 Day @25 C. | 92.6% | 37.4% | 6 | 15.3% |
|  | 3 Days @25 C. | 59.5% | 29.1% | 6 | 11.9% |
|  | 7 Days @25 C. | 44.5% | 21.9% | 6 | 8.9% |
|  | 14 Days @25 C. | 35.0% | 13.8% | 6 | 5.6% |
| LVV1 MVD Duplicate | Drying Yield | 59.3% | 22.3% | 6 | 9.1% |
|  | 1 Day @25 C. | 92.9% | 53.7% | 6 | 21.9% |
|  | 3 Days @25 C. | 65.8% | 22.6% | 6 | 9.2% |
|  | 7 Days @25 C. | 36.0% | 18.0% | 6 | 7.4% |
| LVV1-ST30 MVD Cycle 2 | Drying Yield | 30.7% | 8.7% | 4 | 4.3% |
|  | 1 Day @25 C. | 87.0% | 49.0% | 6 | 20.0% |
|  | 3 Days @25 C. | 74.8% | 24.0% | 5 | 10.7% |
|  | 7 Days @25 C. | 37.7% | 15.2% | 6 | 6.2% |
| LVV1-ST30 Lyo | Drying Yield | 55.4% | 16.4% | 4 | 8.2% |
|  | 1 Day @25 C. | N/A | N/A | N/A | N/A |
|  | 3 Days @25 C. | 11.9% | 2.9% | 4 | 1.4% |
|  | 7 Days @25 C. | N/A | N/A | N/A | N/A |

The final moisture content of product is dependent on cycle parameters (Ramp rate, total power, energy and time) and load, for any given product. Based on relative potency measurement, it can be concluded that the drying yield is lower for a high disaccharide formulation as compared to a low disaccharide formulation but accelerated stability profile is improved. Similarly, drying yield of the microwave vacuuum dried formulation is lower compared to the freeze-dried formulation. Also, the stability, as illustrated in Table 4, suggests improved stability is btained for MV-dried samples compared to freeze-dried samples. It should be noticed, however, that the MVD cycle was not optimized for best drying yield whereas the freeze-drying cycle was optimized.

Long-Term Stability:

Samples were placed at −20, 5, and 15° C. for long-term stability (Timepoints: 0, 1, 3, 6, 9, 12, 18, 24, 30 months; experiment 1 e for Table 1). Plaque assay results, post 1 month incubation, are shown below (1×6 format). Results are shown in Table 5 and FIG. 1.

TABLE 5

Long-term stability of LVV1

Figure 1:
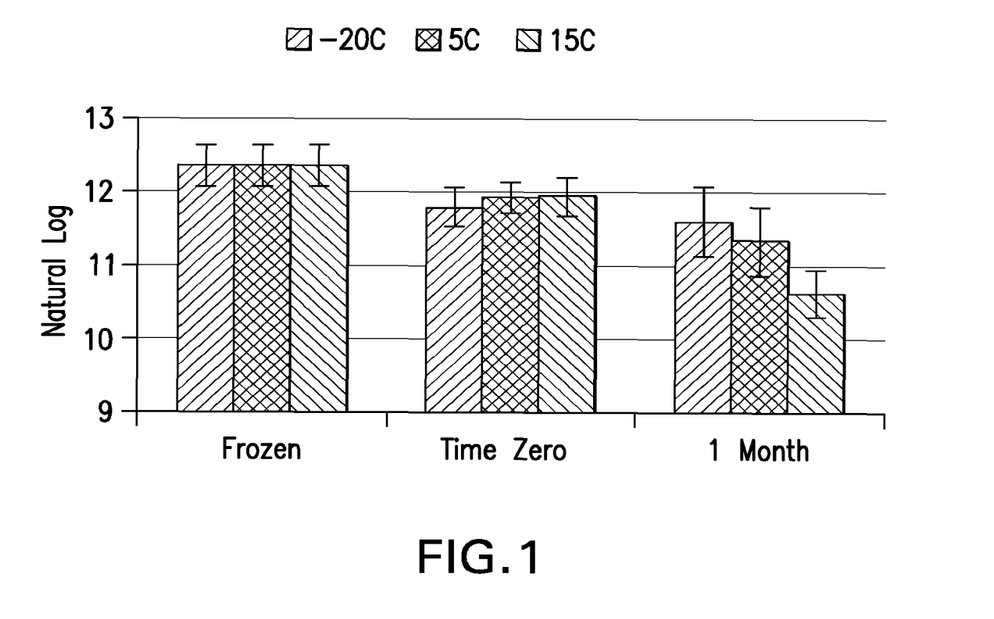
FIG. 1: Real-time storage stability (Frozen, dried and 1-month time points) of an enveloped live-virus vaccines at −20° C., 5° C. and 15° C. is shown.

|  | MVD Yield | 1 Month Yield |
| --- | --- | --- |
| −20 C. | 57.3% ± 10.8% | 88.2% ± 29.7% |
| 5 C. | 66.3% ± 15.5% | 59.9% ± 21.2% |
| 15 C. | 67.8% ± 13.1% | 27.8% ± 8.4% |

These results indicate that the drying yield was similar across the three batches. This gives positive information about the consistency and reproducibility of cycles in the MVD. Dried samples stored at −20° C. were the most stable, while the dried samples stored at 15° C. were the least stable.

These results suggest that under the given experimental conditions (a) LVV1 can be dried in microwave vacuum dryer in a relatively short time (3 hr 10 min-7 hrs in MVD compared to 28-48 hrs for freeze-drying) and (b) the final moisture content of the dried cake can be altered significantly (1.5-3.5% for urea containing and 2.2-4.4% for non-urea containing LVV1 formulation).

Figure 2:
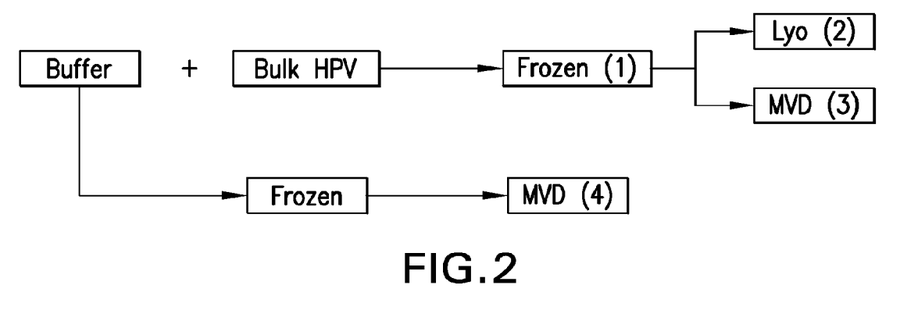
FIG. 2: Experimental design for evaluating immunogenicity of HPV in a Guinea pig model post-drying. Frozen HPV formulation and MVD-dried placebo were used as control.

Example 2: Microwave Vacuum Drying (MVD) of Virus-Like Particles (VLP) in a Glass Vial A guinea pig animal model for 9-valent HPV (See International Patent Application Publication Nos. WO2004/084831, WO2005/032586, WO2005/047315, and WO2005/097821) was used to compare microwave-dried (FIG. 2, MVD(3)), lyophilized (FIG. 2, Lyo(4)), frozen (never dried, (FIG. 2, Frozen(1))) and microwave-dried placebo ((FIG. 2, MVD(4)). ELISA titers for the active study arms were comparable after two doses and identical after three doses.

Specifically, non-adjuvanted, 9-valent HPV was formulated (5% Sucrose, 5% Mannitol, 10 mM L-Histidine, 0.005% PS-80, pH 6.2), filled into vials (1 mL), blast frozen, annealed, and then dried using either conventional lyophilization or microwave vacuum drying. Microwave-dried placebo was also prepared. Particle size (by DLS) and Type 18 Biacore potency results (123% for frozen, 138% for both microwave-dried and lyophilized samples) were comparable across all product types. Residual moisture was 2.2% for lyophilized samples, 2.4% for microwave-dried placebo, and 2.8% for microwave-dried active samples. Samples were transferred subsequently evaluated in the HPV guinea pig animal model.

The guinea pig study consisted of 4 animals in the microwave-dried placebo group and 8 animals in each active arm (frozen, microwave-dried, and lyophilized HPV). A reconstitution and field mix procedure was developed for addition of Merck Alum Adjuvant (MAA) prior to animal dosing, resulting a final vaccine consisting of 46.4 micrograms/mL of HPV and 83.4 micrograms/mL of MAA. Animals were given a 0.2 mL IM injection at 0, 4, and 8 weeks and titers were assessed three weeks after the second and third dose. Although within error bars, marginal titer differences were observed after two doses with the following rank order: frozen (6.6×10E6)>lyophilized (2.9×10E6)>microwave-dried (1.6×10E6). Post-dose three titers in the active groups were nearly identical (8×10E5 for frozen; 7×10E5 for lyophilized and microwave-dried), although slightly slower than post-dose 2 titers.

This study is a controlled, head-to-head comparison of microwave-dried product with lyophilized product in an established animal model. Study results for microwave vacuum dried product and lyophilized products were comparable; therefore, it is concluded that microwave drying did not induce any product changes affecting the guinea pig immune response.

Example 3: Microwave Vacuum Drying (MVD) of Combination Vaccines (High Disaccharide Formulation of a Combination Vaccine Comprising Multiple Live Enveloped Viruses (Vaccine 2))

Compatibility of Vaccine 2 (a combination of live viruses) was evaluated in microwave vacuum drying as a function of formulation composition. Freeze-dried vials were used as controls. All vials were blast frozen prior to drying. Cycle parameters and % moisture post drying are shown below.

TABLE 6

MVD conditions for combination vaccine

| Formulation | Image (Drying) | Cycle Parameters | % Moisture |
|---|---|---|---|
| 12.5% Sucrose/ 12.5% Trehalose | 0.7 ml/3 cc vial (dried using MVD) | 1 magnetron at 50 W for 2 hrs<br>2 magnetrons at 80 W each for 1 hr<br>2 magnetrons at 130 W each for 1 hr<br>2 magnetrons at 250 W each for 45 min<br>2 magnetrons at 350 W each for 45 min<br>2 magnetrons at 450 W each for 1 hr 45 min<br>2 magnetrons at 375 W each for 1 hr 30 min<br>Total Time: 8 hrs 45 min<br>Total Energy: 3.98 kWh | 3.82 |
| | 0.7 ml/3 cc vial (dried using Lyo) | Freezing/vacuum pull: −50° C./54 mtorr<br>Primary Drying: −35.1° C. for 10080 min at 54 mtorr with a ramp rate of 1.5 C/min<br>Secondary Drying: 0° C. for 300 min at 54 mtorr with a ramp rate of 0.5 C/min | 4.78 |
| 25% Trehalose | 0.7 ml/3 cc vial (dried using MVD) | 2 magnetrons at 55 W each for 90 min<br>2 magnetrons at 60 W each for 24 min<br>2 magnetrons at 70 W each for 15 min<br>2 magnetrons at 80 W each for 15 min<br>2 magnetrons at 90 W each for 15 min<br>2 magnetrons at 100 W each for 15 min<br>2 magnetrons at 120 W each for 15 min<br>2 magnetrons at 150 W each for 60 min<br>2 magnetrons at 200 W each for 40 min<br>2 magnetrons at 250 W each for 30 min<br>2 magnetrons at 300 W each for 60 min<br>2 magnetrons at 350 W each for 45 min<br>2 magnetrons at 400 W each for 45 min<br>2 magnetrons at 450 W each for 20 min<br>2 magnetrons at 375 W each for 40 min<br>Total Time: 8 hrs 49 min<br>Total Energy: 3.6 kWh | 3.94 |

These results suggests that under the given experimental conditions high disaccharide formulations of Vaccine 2 can be dried in microwave vacuum dryer in a relatively short time (9 hrs in MVD compared to ~175 hrs for freeze-drying). This is an example of drying a combination vaccine in microwave vacuum drying.

Example 4: Evaluation of MVD Technology for Drying a High Disaccharide Formulation in a Dual Cartridge Device A formulation containing 25% trehalose was dried in a dual cartridge device image in <6 hours using microwave vacuum drying in a manner that the dried cakes look indistinguishable from a freeze-dried cake in appearance. Specifically, a total of 40 dual cartridge devices were filled with 0.3 mL of the high disaccharide formulations. Syringes were blast frozen and were dried using microwave under vacuum (30-40 mTorr). MVD cycle was stopped at a terminal temperature of 23° C. and a total energy of 1.28 kWh. The total cycle time was 5 hrs and 16 minutes.

This example shows successful microwave vacuum drying of high disaccharide formulation in a dual cartridge device in less than 6 hours.

Example 5: Evaluation of the Microwave Vacuum Drying Compatibility of GRAS (Generally Regarded As Safe) Excipients at Various Concentrations Samples evaluated for MVD are shown below along with their respective concentrations (w/v). Each formulation consisted of a 0.5 ml fill in a 3 cc vial.
3) Sucrose, 5%
5) Sucrose, 15%
6) Sucrose, 20%
7) Sucrose, 25%
8) Trehalose, 5%
9) Trehalose, 10%
10) Trehalose, 15%
11) Trehalose, 20%
12) Trehalose, 25%
13) Dextran, 3%
14) Sorbitol, 3%
15) 150 mM NaCl
16) Glycine 2%
17) Trehalose, 25%+3% Sorbitol
18) Trehalose, 25%+3% Sorbitol+150 mM NaCl
19) Trehalose, 25%+3% Dextran
20) Trehalose, 25%+Glycine 2%

Samples were blast frozen and subjected to microwave vacuum drying using the cycle parameters as shown below:
Samples 3, 5-13, 16-20
1 mag, 400 W, 1 hr
2 mag, 400 W ea., 40 min
3 mag, 400 W ea., 30 min
4 mag, 400 W ea, 30 min Post-drying, samples were tested for moisture content using Karl Fischer.
Results:

TABLE 7

MVD of GRAS

| Sample # | Sample | # of vials available | Vial & Stopper Weight (g) | Vial, Stopper, Sample Weight (g) | Net weight (g) | % Moisture |
|---|---|---|---|---|---|---|
| 3 | Sucrose, 5% | 3 | 9.8223 | 9.841 | 0.0187 | 2.34 |
| 5 | Sucrose, 15% | 4 | 9.7298 | 9.7728 | 0.043 | 1.71 |
| 6 | Sucrose, 20% | 4 | 9.6389 | 9.7212 | 0.0823 | 2.20 |
| 7 | Sucrose, 25% | 4 | 9.6027 | 9.6976 | 0.0949 | 1.06 |
| 8 | Trehalose, 5% | 4 | 9.7064 | 9.7219 | 0.0155 | 5.38 |
| 9 | Trehalose, 10% | 4 | 9.6138 | 9.6416 | 0.0278 | 4.33 |
| 10 | Trehalose, 15% | 4 | 9.7093 | 9.7551 | 0.0458 | 3.10 |
| 11 | Trehalose, 20% | 4 | 9.7344 | 9.7967 | 0.0623 | 2.64 |
| 12 | Trehalose, 25% | 4 | 9.55 | 9.629 | 0.079 | 2.90 |
| 13 | Dextran, 3% | 4 | 9.6388 | 9.651 | 0.0122 | 3.84 |
| 14 | Sorbitol, 3% | 0 | N/A | N/A | N/A | |
| 15 | 150 mM NaCl | 0 | N/A | N/A | N/A | |

TABLE 7-continued

MVD of GRAS

| Sample # | Sample | # of vials available | Vial & Stopper Weight (g) | Vial, Stopper, Sample Weight (g) | Net weight (g) | % Moisture |
|---|---|---|---|---|---|---|
| 16 | Glycine 2% | 3 | 9.6898 | 9.6987 | 0.0089 | 4.91 |
| 17 | Trehalose, 25% + 3% Sorbitol | 4 | 9.7271 | 9.8132 | 0.0861 | 3.17 |
| 18 | Trehalose, 25% + 3% Sorbitol + 150 mM NaCl | 4 | 9.6156 | 9.7124 | 0.0968 | 1.09 |
| 19 | Trehalose, 25% + 3% Dextran | 3 | 9.7396 | 9.8379 | 0.0983 | 3.37 |
| 20 | Trehalose, 25% + Glycine 2% | 4 | 9.8515 | 9.9435 | 0.092 | 3.92 |

CONCLUSIONS

1. Microwave vacuum drying is compatible with vial drying of various excipients such as sucrose, trehalose, sorbitol, NaCl Glycine etc. (it should be noted that a general MVD cycle was used and all test formulations were loaded in the same batch i.e. cycle was not optimized for individual formulation).
2. Additional bulking agents are required for drying sorbitol containing or salt containing formulations as these cakes collapsed on MVD in absence of other excipients.
3. Moisture ranges for MVD dried formulation, in the current study, ranged from 1.1-5.4%.

OVERALL SUMMARY

Even though this drying process is compatible with commonly used pharmaceutical sugars such a sucrose, trehalose, raffinose, mannitol, lactose etc.; drying of sugars or salts with low glass transition (such as sorbitol, NaCl containing formulation etc.) requires addition of other bulking agents to provide cake structure. The MVD approach described herein is able to dry >20% solid containing formulations in <12 hrs.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A method for drying a vaccine composition comprising a virus or viral protein subunit or virus-like particles comprising the steps of:
  a) providing an aqueous composition in a primary container comprising a buffer, the virus or viral protein subunit or virus-like particles, and between about 20% w/w and about 60% w/w of one or more non-polymeric sugars;
  b) freezing the composition, thereby forming at least one frozen body comprising the buffer in frozen form; and
  c) applying microwave radiation in a traveling wave format at a power in a range of between 0.5 and 8 KW/hr/Kg to the frozen body under a pressure below atmospheric pressure to produce a dried formulation.

2. The method according to claim 1, wherein the composition is sublimated in less than 12 hours.

3. The method according to claim 1, wherein the composition is sublimated in 3 to 8 hours.

4. The method according to claim 1, wherein the pressure is in the range of 20 to 500 mTorr.

5. The method according to claim 4, wherein the pressure is in the range of 20 to 200 mTorr.

6. The method according to claim 1, wherein the temperature of the composition in step c) does not exceed 45° C.

7. The method according to claim 1, wherein the temperature of the composition in step c) does not exceed 35° C.

8. The method according to claim 1, wherein the amount of the sugar in the aqueous composition is chosen from the group that consists of the ranges 20-55% w/w, 20-50% w/w, 20-45% w/w, 25-45% w/w, 25-47.5% w/w, 25-40% w/w, 30-47.5% w/w, 30-40% w/w, 25-35% w/w or 27-30% w/w.

9. The method according to claim 1, characterised in that the sugar comprises monomeric and/or dimeric molecules.

10. The method according to claim 9, wherein the sugar is glucose, galactose, maltose, sucrose, trehalose, fructose, lactose, saccharose, mannitol, sorbitol, xylitol or a combination thereof.

11. The method according to claim 1, wherein the vaccine is a combination vaccine.

12. The method according to claim 1, wherein the vaccine is an enveloped virus vaccine.

13. The method according to claim 1, wherein the primary container is selected from glass vial, resin vials, plastic vials, dual cartridge device, or foil-pouch based devices vaccine.

14. The method according to claim 1, wherein the moisture content of the composition after drying is less than 6.0%.

15. The method according to claim 1, wherein the dried product formed comprises the vaccine dispersed in a solid matrix of a non-polymeric sugar.

16. The method according to claim 1, wherein the composition is flash frozen.

17. The method according to claim 12, wherein the enveloped virus is live.

18. The method according to claim 12, wherein the enveloped virus is selected from cytomegalovirus, herpes simplex virus, measles, mumps, respiratory syncytial virus, rotavirus, rubella, dengue and varicella.

19. The method according to claim 1, wherein the ratio of power distribution between the first half cycle and total drying power is 15% to 50%.

20. The method according to claim 1, wherein the ratio of power distribution between the first half cycle and total drying power is 15% to 30%.

* * * * *